United States Patent [19]

Moriya et al.

[11] Patent Number: 5,055,501
[45] Date of Patent: Oct. 8, 1991

[54] PROCESS FOR PRODUCING HIGHLY WATER-ABSORBING RESINS FROM DIEPOXIDES AND ACRYLIC POLYMERS

[75] Inventors: Tetsuo Moriya, Hirakata; Susumu Kondo, Kyoto, both of Japan

[73] Assignee: Nippon Gohsei Kagaku Kogyo Kabushiki Kaisha, Osaka, Japan

[21] Appl. No.: 331,789

[22] Filed: Apr. 3, 1989

[30] Foreign Application Priority Data

Nov. 6, 1986 [JP] Japan .................... 61-264831

[51] Int. Cl.$^5$ .................... C08F 20/04; C08F 2/16
[52] U.S. Cl. .................... 523/409; 523/407; 523/411; 523/412; 523/423; 523/119; 525/119; 527/300; 527/311; 527/313
[58] Field of Search ........... 523/409, 411, 412, 407, 523/423; 525/119; 527/300, 311, 313

[56] References Cited

U.S. PATENT DOCUMENTS

| | | | |
|---|---|---|---|
| 3,947,396 | 3/1976 | Kangas et al. | 523/413 |
| 3,966,679 | 6/1976 | Gross | 525/119 |
| 4,340,706 | 7/1982 | Obayashi et al. | 526/207 |
| 4,351,922 | 9/1982 | Yoshida et al. | 525/116 |
| 4,446,261 | 5/1984 | Yamasaki et al. | 524/40 |
| 4,541,871 | 9/1985 | Obayashi et al. | 525/60 |
| 4,666,975 | 5/1987 | Yamasaki et al. | 524/733 |

FOREIGN PATENT DOCUMENTS 3737196 12/1990 Fed. Rep. of Germany.

*Primary Examiner*—John Kight, III
*Assistant Examiner*—Frederick Krass
*Attorney, Agent, or Firm*—Armstrong, Nikaido, Marmelstein, Kubovcik & Murray

[57] ABSTRACT

A process is provided for the production of a highly water-absorbing resin comprising a polymer obtained by polymerizing a monomer composition mainly composed of an ethylenically unsaturated monocarboxylic acid and/or an alkali metal salt thereof. The process comprises incorporating an oil-soluble polyfunctional epoxy compound having a solubility in 100 g of water at 20° C. of not more than 0.3 g into the polymer by adding 0.0005-3 parts by weight of the oil-soluble polyfunctional epoxy compound to 100 parts by weight of the polymer or the monomer composition to be subjected to polymerization and thereby causing crosslinking.

1 Claim, No Drawings

PROCESS FOR PRODUCING HIGHLY WATER-ABSORBING RESINS FROM DIEPOXIDES AND ACRYLIC POLYMERS

This is a division of application Ser. No. 116,831, filed Nov. 5, 1987, now abandoned.

BACKGROUND OF THE INVENTION

1. Technical Field

This invention relates to a process for producing highly water-absorbing resins improved in absorbency for water and body fluids and furthermore improved in strength in the state of a swollen gel.

2. Prior Art

Known resins capable of absorbing water in large amounts include such highly water-absorbing resins as partially hydrolyzed starch-acrylonitrile graft polymers, partially neutralized polyacrylic acid species, polyethylene oxide species, partially hydrolyzed polyacrylonitrile species and polyvinyl alcohol species. Among them, partially neutralized polyacrylic acid species are particularly useful.

These highly water-absorbing resins are used in various fields, for example as body fluid absorbents, which absorb body fluids and prevent them from leaking, in sanitary products such as sanitary napkins, tampons, diapers and so on, and further as seed coverings, water leak stoppers, thickening agents, dew formation inhibitors, sludge coagulants, driers, moisture conditioners, etc.

Such highly water-absorbing resins should meet the following requirements: that when they are brought into contact with water or body fluids, the phenomenon of lump formation should not take place, that they should have great absorbencies for water and body fluids with high rates of absorption, and that the gels formed upon absorption of water or a body fluid by them should have great strength. Even partially neutralized polyacrylic acid, which is one of preferred highly water-absorbing resins, cannot always meet these requirements.

Therefore, various attempts have been made to improve the absorbency and gel strength of partially neutralized polyacrylic acid by carrying out crosslinking with a crosslinking agent such as ethylene glycol diglycidyl ether in the step of polymerization or after polymerization. Such attempts are listed below.

Japanese Kokai Tokkyo Koho No. 44627/1982: Said polymer is dispersed in a mixed solvent composed of water and a hydrophilic organic solvent, with a crosslinking agent having two or more functional groups, and crosslinking is carried out.

Japanese Kokai Tokkyo Koho No. 42602/1983: Said polymer is dispersed in a dispersion medium and brought into contact with a crosslinking agent, whereby the polymer is crosslinked on the grain surface thereof.

Japanese Kokai Tokkyo Koho No. 117222/1983: Said polymer is crosslinked with a crosslinking agent having two or more functional groups in an inert solvent in the presence of water.

Japanese Kokai Tokkyo Koho No. 62665/1984: Said polymer is crosslinked in a hydrated form with a crosslinking agent having two or more functional groups.

Japanese Kokai Tokkyo Koho No. 147475/1985: Said polymer is crosslinked with a crosslinking agent having two or more functional groups in a hydrophilic inert solvent in the presence of water and a mineral powder.

Japanese Kokai Tokkyo Koho No. 177004/1985: Said polymer is crosslinked with a crosslinking agent in an inert solvent in the presence of a hydrophilic polyhydric alcohol and a mineral powder.

Japanese Kokai Tokkyo Koho No. 186506/1985: In subjecting a dispersion or a suspension of an aqueous monomer solution in a hydrocarbon or halogenated aromatic hydrocarbon to polymerization, an oil-soluble cellulose ester or cellulose ether is used. After polymerization, the moisture content is adjusted and crosslinking is carried out using a crosslinking agent having two or more functional groups.

Japanese Kokai Tokkyo Koho No. 199010/1985: The monomer is polymerized in the presence of a specific polycationic epoxy compound (a reaction product of an imidazole and a halomethyloxirane compound).

Japanese Kokai Tokkyo Koho No. 255814/1985: A mixture of the polymer and a mineral powder is sprayed, with stirring, with a crosslinking agent and water, the crosslinking reaction is effected by heating and, thereafter, water is distilled off.

Japanese Kokai Tokkyo Koho No. 69812/1986: During or after polymerization of the monomer, a monoglycidyl compound is subjected to reaction.

PROBLEMS SOLVED BY THE INVENTION

However, investigations by the present inventors have revealed that the grains obtained by reacting partially neutralized polyacrylic acid with a crosslinking agent such as ethylene glycol diglycidyl ether in accordance with the teachings above have drawbacks such as the following:

(a) That when they are brought into contact with water, they are partly dissolved in water in amounts that are not negligible;

(b) That they are not fully satisfactory in respect to absorption rate, lump formation prevention and gel strength although they are satisfactory with respect to ultimate absorbency for body fluids.

The present inventors supposed that the use of such hydrophilic crosslinking agents as ethylene glycol diglycidyl ether might place a limit on the improvement in performance characteristics of partially neutralized polyacrylic acid by the known methods listed hereinabove. Accordingly, they conducted intensive investigations into the effects of hydrophobic crosslinking agents, which were used contrary to the known methods, and, as a result, they have now completed the Present invention.

SUMMARY OF THE INVENTION

The relates to a process for the production of a highly water-absorbing resin comprising polymerizing a polymer obtained to from a monomer composition mainly composed of an ethylenically unsaturated monocarboxylic acid and/or an alkali metal salt thereof, incorporating an oil-soluble polyfunctional epoxy compound having a solubility in 100 g of water at 20° C. of not more than 0.3 g into said polymer by adding 0.0005-3 parts by weight of the oil-soluble polyfunctional epoxy compound to 100 parts by weight of the polymer or the monomer composition to be subjected to polymerization and thereby causing crosslinking.

DETAILED DESCRIPTION OF THE INVENTION

The invention is described below in further detail.

MONOMERS

As the ethylenically unsaturated monocarboxylic acid and/or its alkali metal salt, there may be mentioned acrylic acid, methacrylic acid and crotonic acid, and the sodium, potassium or ammonium salt of these acids. Partially neutralized acrylic acid salt is of particular importance.

Side by side with these monomer components, ethylenically unsaturated monocarboxylic acid esters, ethylenically unsaturated dicarboxylic acid and salts, anhydrides and esters thereof, vinyl esters, vinyl ethers, acrylamide, methacrylamide, and the like can be used as comonomers. Starch, cellulose, a derivative of starch or cellulose, polyvinyl alcohol, or the like may be used simultaneously for graft polymerization.

OIL-SOLUBLE POLYFUNCTIONAL EPOXY COMPOUND

In accordance with the invention, an oil-soluble polyfunctional epoxy compound is incorporated into the polymers obtained by polymerization of the above-mentioned monomers as a component of said polymers by reacting said oil-soluble polyfunctional epoxy compound with said polymers or the monomers to be subjected to polymerization.

Useful as the oil-soluble polyfunctional epoxy compound are such epoxy compounds having a solubility in 100 g of water at 20° C. of not more than 0.3 g. When said solubility exceeds 0.3 g, the product polymers will be unsatisfactory in respect to gel strength, with other performance characteristics becoming unbalanced.

As typical examples of such oil-soluble polyfunctional epoxy compounds, there may be mentioned the following:

(a) Alicyclic epoxy compounds, in particular the compound of the structural formula.

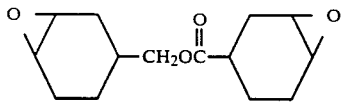

The above compound is commercially available, for example from Daicel Ltd. under the trademark CELOXIDE 2021. The solubility of this compound in 100 g of water is 0.03 g at 20° C.

(b) Condensation products from a long-chain dibasic acid and epichlorohydrin, in particular compounds having the following structural formula:

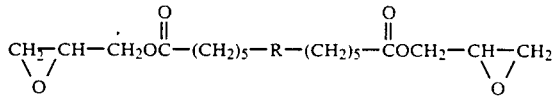

In the above formula, —R— is, for example,

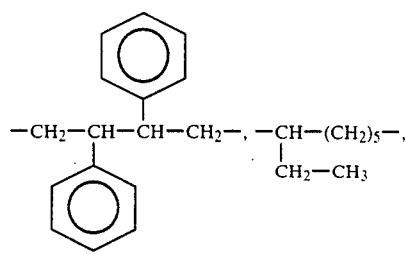

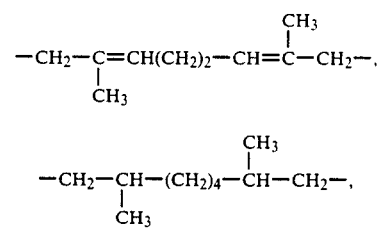

or an equimolar mixture of —CH$_2$—CH=CH—(CH$_2$)$_2$—CH=CH—CH$_2$— and

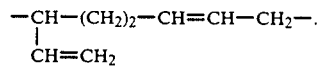

As commercially available products, there are OS RESINS having code-numbers 101, 102, 103, 104 and 105 supplied by Okamura Seiyu K. K. The solubility of these compounds in 100 g of water is substantially zero at 20° C.

(c) Reaction products from bisphenol A and an epichlorohydrin type epoxy compound, in particular products having the following structural formula

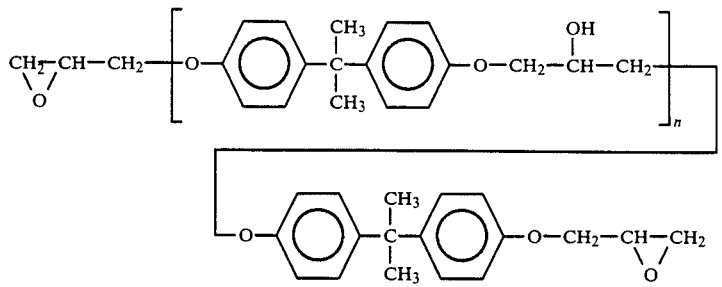

As a commercial product, there may be mentioned EPIKOTE 828 available from Yuka-Shell Epoxy Co. Ltd. The solubility of this product in 100 g of water is 0.01 g at 20° C.

It should be noted that the above-mentioned examples of the oil-soluble polyfunctional epoxy compounds serve only to illustrate and that any oil-soluble polyfunctional epoxy compound having a solubility in 100 g of water at 20° C. of not more than 0.3 g is suitable for the purpose of this invention.

The oil-soluble polyfunctional epoxy compound is incorporated into the above-mentioned polymer by reacting said compound with the polymer or the monomer composition to be subjected to polymerization in a quantity ratio of 0.0005-3 part by weight of said compound to 100 parts by weight of the polymer or monomer composition.

When the oil-soluble polyfunctional epoxy compound is used in an amount less than 0.0005 part by weight on the above basis, the effect of crosslinking cannot be produced, hence the gel strength remains low. When, conversely, the amount of said compound exceeds 3 parts by weight, the density of crosslinking becomes excessive and, as a result, the absorbency for water decreases.

The particularly preferred range of amounts of the oil-soluble polyfunctional epoxy compound varies depending on the type or kind thereof and is, for example, 0.001-0.1 part by weight in the case of alicyclic epoxy compounds such as mentioned above under (a), 0.1-1 part by weight in the case of long-chain dibasic acid-epichlorohydrin condensation products such as mentioned above under (b), and 0.1-1 part by weight in the case of bisphenol A epichlorohydrin type epoxy compound reaction products mentioned above under (c), per 100 parts by weight of polymer. The compounds mentioned above under (a) are particularly preferred since they are rich in reactivity and, hence, can achieve the object of the invention at a low level of addition and in a short reaction period.

INCORPORATION OF THE OIL-SOLUBLE POLYFUNCTIONAL EPOXY COMPOUND INTO THE POLYMER

The oil-soluble polyfunctional epoxy compound can be incorporated into the polymer in any of the following modes:

(1) The oil-soluble polyfunctional epoxy compound is mixed with the polymer obtained by polymerization of one or more of the above-mentioned monomers and the mixture is heated for the progress of reaction;

(2) The oil-soluble polyfunctional epoxy compound is added to a hydrophobic medium, an aqueous monomer solution is then suspended in the hydrophobic medium, and the polymerization is carried out in the manner of reversed-phase suspension polymerization;

(3) The oil-soluble polyfunctional epoxy compound is dispersed in an aqueous monomer solution and this aqueous solution is either subjected to stationary polymerization or suspended in a hydrophobic medium and subjected to reversed-phase suspension polymerization.

In the above mode (1), the polymer is first prepared from a monomer composition mainly composed of an ethylenically unsaturated monocarboxylic acid and/or an alkali metal salt thereof by an appropriate method of polymerization as selected optionally.

For example, the method comprising polymerizing said monomer composition in an aqueous medium in the presence of a persulfate salt. In that case, the polymerization temperature is suitably about 55-90° C.

Another method suited for use comprises suspending an aqueous solution of the above-mentioned monomer composition in a hydrophobic medium and carrying out the polymerization in the manner of reversed-phase suspension polymerization. Useful as the hydrophobic medium are hexane, cyclohexane, benzene, toluene, xylene, and the like. The catalyst and chain transfer agent are added to the monomer-containing aqueous solution. The polymerization temperature is suitably within the range of from about 50° C. to the refluxing temperature of the system.

The polymer thus obtained by polymerization is admixed with the oil-soluble polyfunctional epoxy compound and the mixture is heated for reaction. To obtain a homogeneous state of the mixture, it is preferable to effect the mixing by spraying a solution of the oil-soluble polyfunctional epoxy compound with an appropriate hydrophobic solvent such as a hydrocarbon solvent onto moistened or wetted polymer grains. Although the polymer to be submitted to heat treatment may be in a dry state, the reaction proceeds more smoothly when the polymer contains about 1-70% by weight, preferably about 3-50% by weight, of water.

The heating is conducted at a temperature of 50-200° C., preferably 70-160° C., for a few minutes to several hours, preferably 3 minutes to 2 hours. When an alicyclic epoxy compound is used as the oil-soluble polyfunctional epoxy compound, a heating period of at most about 1 hour is sufficient.

In the above mode (2), an aqueous solution of the above-mentioned monomer composition is suspended in a hydrophobic medium and reversed-phase suspension polymerization is carried out.

The oil-soluble polyfunctional epoxy compound is added to the hydrophobic medium.

The catalyst and chain transfer agent are added to the aqueous monomer solution.

The polymerization temperature is suitably within the range of from about 50° C. to the refluxing temperature of the system.

In the above mode (3), an aqueous solution of the above-mentioned monomer composition is either subjected as it is to stationary polymerization or suspended in a hydrophobic medium and subjected to reversed-phase suspension polymerization.

The oil-soluble polyfunctional epoxy compound is dispersed in the monomer-containing aqueous solution. For facilitating dispersion of said compound on that occasion, it is advisable to add, together with a dispersing agent (e.g. a nonionic surfactant), the oil-soluble polyfunctional epoxy compound, with or without dilution with a hydrophobic solvent. The aqueous solution is then thoroughly mixed.

The catalyst and chain transfer agent are added to the monomer-containing aqueous solution.

The polymerization temperature is suitably within the range of from about 50° C. to the refluxing temperature of the system.

When required, granular inorganic substances and/or other additives may be incorporated into the thus-obtained crosslinked polymer granules. As the granular inorganic substances, there may be mentioned silicon oxide, aluminum oxide, titanium oxide, zinc oxide, calcium silicate, magnesium silicate, clay, talc, kaolin, calcium carbonate, barium carbonate and barium sulfate, among others.

The highly water-absorbing resins according to the invention which comprise the crosslinked polymers obtained in the above manner are suited for use as body fluid absorbents in sanitary or hygienic products for absorbing body fluids and preventing leakage of such fluids, and further as seed coverings, water leak stoppers, thickening agents, dew formation inhibitors, sludge coagulants, driers, moisture content conditioners, and so forth.

WORKING AND EFFECTS OF THE INVENTION

Supposedly, the oil-soluble polyfunctional epoxy compound, which is used in accordance with the invention, provides the polymer with a crosslinked structure and at the same time gives a slight degree of hydrophobicity to the polymer.

As a result of introduction of the oil-soluble polyfunctional epoxy compound into the polymer, the polymer acquires a network structure which can retain water or body fluids in large amounts. The retention volume, namely the absorbency, is quite comparable to that attainable by providing the same polymer with a crosslinked structure using a hydrophilic polyfunctional epoxy compound as the crosslinking agent.

Furthermore, since the polymer is provided with a slight degree of hydrophobicity on the occasion of network formation, the problem regarding the inability of water to penetrate into the networks due to dissolution or excessive swelling of the polymer grain surface upon contact of said polymer with water or body fluids is remedied; as a result, lump formation is prevented efficiently and easy and rapid penetration of water into the network becomes possible.

The fact that the polymer acquires a slight degree of hydrophobicity contributes to marked reduction in the dissolution of polymer grains in water upon their contact with water and this property is also conducive to marked improvement in strength of the swollen gel formed upon absorption of water or a body fluid.

The highly water-absorbing resins comprising the crosslinked polymers obtained by the process according to the invention are superior in each of such performance characteristics as absorbency, insolvability in water, reduced tendency toward lump formation, absorption rate and gel strength and therefore are very useful as body fluid absorbents for use in sanitary or hygienic products and also can be used in other various applications.

EXAMPLES

The following examples are further illustrative of the present invention. Hereinafter, "part(s)" and "%" are on the weight basis.

POLYMER PRODUCTION

Production Example 1

A 500-ml flat-bottomed separable flask equipped with a stirrer, a reflux condenser and a nitrogen gas inlet was charged with 40 g of acrylic acid (special reagent grade). Then, a solution of 17.9 g of 95% pure sodium hydroxide in 53 g of water was added dropwise gradually to the charge with stirring and cooling to thereby effect neutralization. The flask contents were bubbled with nitrogen for 30 minutes for purging dissolved oxygen and air from the flask.

Then, 0.4 ml of a 1% aqueous ammonium persulfate solution bubbled with nitrogen in advance was added and, after thorough mixing, stirring was discontinued.

Polymerization was started without stirring by immersing the flask in a bath maintained at 60° C. The flask contents temperature reached a maximum of 80° C. in 10 minutes, and then lowered to 60° C. After maintaining this temperature for 1 hour, the polymerization reaction was terminated by cooling the mixture to room temperature.

The contents were taken out from the flask, cut to pieces and dried in a vacuum drier at 100° C. for 2 hours. The subsequent comminution on a crusher gave a polymer product 40–200 mesh in grain size.

Polymer Production Example 2

A 500-ml flat-bottomed separable flask A equipped with a stirrer, a reflux condenser and a nitrogen gas inlet was charged with 300 ml of n-hexane and 2.4 g of sorbitan monostearate and purged of dissolved oxygen and air in the flask by nitrogen bubbling for 30 minutes.

Another separable flask B was charged with 40 g of acrylic acid (special reagent grade). Then, a solution of 17.9 g of 95% pure sodium hydroxide in 53 g of water was added dropwise gradually with stirring to effect neutralization. Dissolved air was purged by nitrogen bubbling with stirring. Thereafter, 0.4 ml of a 1% aqueous persulfate solution and 0.2 g of a 0.5% aqueous N,N'-methylenebisacrylamide solution, each bubbled with nitrogen in advance, were added and thorough mixing was carried out.

The contents of the flask B were transferred to the above-mentioned separable flask A while care was used not to allow said contents to contact with air.

After the transfer, the flask A was immersed in a bath and heated at 60–62° C. with stirring for 4 hours for polymerization. The water was then distilled off azeotropically with n-hexane.

After cooling, the contents were filtered through a 325-mesh wire gauze, and the solid product was washed with warm n-hexane and air-dried at 80° C.

CROSSLINKED POLYMER PRODUCTION

EXAMPLE 1

The granular polymer obtained in Polymer Production Example 1 was conditioned to a moisture content of 8%, and 100 parts (on the dry basis) of the so-conditioned granular polymer was sprayed, with stirring, with a solution of 0.01 part of an alicyclic epoxy compound having the formula given below (CELOXIDE 2021, Daicel Ltd.; solubility in 100 g of water: 0.03 g at 20° C.), which was used as an example of the oil-soluble polyfunctional epoxy compound, in 10 parts of n-hexane, and the crosslinking reaction was caused to proceed by stirring at 100° C. for 1 hour.

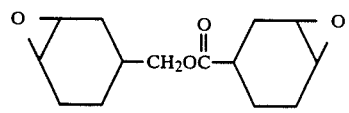

Example 2

The granular polymer obtained in Polymer Production Example 1 was conditioned to a moisture content of 8%, and 100 parts (on the dry basis) of this granular polymer was sprayed, with stirring, with a solution of 0.3 part of a long-chain dibasic acid-epichlorohydrin condensation product of the formula given below (OS RESIN-102, Okamura Seiyu K. K.; insoluble in water) in parts of n-hexane, and the crosslinking reaction was caused to proceed by stirring at 100° C. for 3 hours.

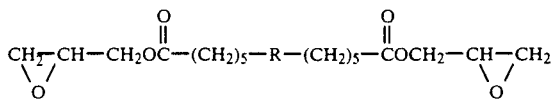

In the above formula, —R— is

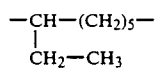

Example 3

The granular polymer obtained in Polymer Production Example 1 was conditioned to a moisture content of and 100 parts (on the dry basis) of the so-conditioned polymer was sprayed, with stirring, with a solution of 0.01 part of CELOXIDE 2021 in 1 part of n-hexane, and stirring was continued at 100° C. for 0.5 hour for the progress of the crosslinking reaction.

Example 4

The granular polymer obtained in Polymer Production Example 2 was conditioned to a moisture content of 20%, and 100 parts (on the dry basis) of the conditioned polymer was sprayed, with stirring, with a solution of 0.006 part of CELOXIDE 2021 in 6 parts of n-hexane, and stirring was continued at 100° C. for 1 hour for the progress of crosslinking.

Example 5

The granular polymer obtained in Polymer Production Example 2 was conditioned to a moisture content of 30%, and 100 parts (on the dry basis) of the granular polymer thus conditioned was sprayed, with stirring, with a solution of 0.006 part of CELOXIDE 2021 in 6 parts of n-hexane, and stirring was continued at 100° C. for 1 hour for the progress of crosslinking.

Example 6

The granular polymer obtained in Polymer Production Example 2 was conditioned to a moisture content of 20%, and 100 parts (on the dry basis) of the so-conditioned granular polymer was sprayed, with stirring, with a solution of 0.3 part of a reaction product from bisphenol A and an epichlorohydrin type epoxy compound (EPIKOTE 828, Yuka-Shell Epoxy Co., Ltd.; solubility in 100 g of water: 0.01 g at 20° C.) in 30 parts of n-hexane, and stirring was continued at 100° C. for 3 hours for the progress of crosslinking.

Example 7

The procedure of Polymer Production Example 2 was followed except that the separable flask A was first charged with 300 ml of n-hexane, 2.4 g of sorbitan monostearate and 0.04 g of CELOXIDE 2021.

Example 8

The procedure of Polymer Production Example 2 was followed except that the neutralization of acrylic acid in the separable flask B with sodium hydroxide was followed by addition of a dispersion of 0.04 g of CELOXIDE 2021 in 4 g of an n-hexane solution containing 1% of polyoxyethylene nonylphenyl ether having an HLB value of 12.

Comparative Example 1

The procedure of Example 3 was followed except that a solution of 0.01 part of ethylene glycol diglycidyl ether, an example of water-soluble polyfunctional epoxy compound, in 10 parts of water was used as the spraying solution in lieu of the solution of CELOXIDE 2021 in n-hexane.

Comparative Example 2

The procedure of Example 3 was followed except that a solution of 0.3 part of ethylene glycol diglycidyl ether in 20 parts of water was used as the spraying solution in lieu of the solution of CELOXIDE 2021 in n-hexane.

Comparative Example 3

The procedure of Example 4 was followed except that a solution of 0.01 part of ethylene glycol diglycidyl ether in 20 parts of water was used as the spraying solution in lieu of the solution of CELOXIDE 2021 in n-hexane.

CHARACTERISTICS MEASUREMENT

The crosslinked polymers obtained in Examples 1–8 and Comparative Examples 1–3 were evaluated for several performance characteristics. The polymer obtained in Polymer Production Example 1 (Reference Example 1) and that obtained in Polymer Production Example 2 (Reference Example 2) were also examined for the same characteristics as controls.

The results obtained are shown below in Table 1.
The measurement conditions used are as follows:

ABSORBENCY FOR AND DISSOLUTION IN DEIONIZED WATER

In a 500-ml beaker is placed 0.2 g (on the dry basis) of the granular polymer or crosslinked granular polymer. Then, 200 g of deionized water is added and the mixture is stirred gently for a short while with a glass rod, then allowed to stand at room temperature for 1 hour, and filtered through a 325-mesh wire gauze. The weight of the gel remaining on the wire gauze and the weight of the solid obtained after evaporation of the filtrate to dryness are measured, and the absorbency and dissolution are calculated as follows:

Absorbency = (remaining gel weight (g) − 0.2)/0.2
Dissolution = filtrate evaporation residue weight (g) × 100/0.2

ABSORBENCY FOR PHYSIOLOGICAL SALINE

In a 500-ml beaker is placed 0.2 g (on the dry basis) of the granular polymer or crosslinked granular polymer. Then, 60 g of physiological saline (0.9% aqueous sodium chloride solution) is added. After stirring gently for a short while with a glass rod, the mixture is allowed to stand at room temperature for 1 hour and then filtered through a 325-mesh wire gauze. The gel remaining on the wire gauze is weighed, and the absorbency is calculated as follows:

Absorbency = (remaining gel weight (g) − 0.2)/0.2

RATE OF ABSORPTION OF PHYSIOLOGICAL SALINE AND OCCURRENCE OR NONOCCURRENCE OF LUMP FORMATION

In a glass vessel having an inside diameter of 30 mm, there is placed 0.2 g (on the dry basis) of the granular polymer or crosslinked granular polymer, followed by addition of 10 g of physiological saline (0.9% aqueous sodium chloride solution) from a measuring pipet. A stopwatch is started simultaneously with the addition, and the time until the polymer grains stop moving is measured. The absorption rate is expressed in terms of the time thus measured. A smaller value means a higher rate of absorption.

On that occasion, judgment is formed by the eye about the occurrence or nonoccurrence of lump formation.

GEL STRENGTH 0.5 g of the gel remaining on the wire gauze as obtained in the measurement of absorbency for physiological saline is placed on the palm of one hand and crushed by rubbing both palms together until the gel turns into a high-viscosity liquid as a result of the granular gel. The number of rubbings required is recorded. A greater number of rubbings means a higher degree of gel strength.

TABLE 1

|  | Deionized water | | Physiological saline | | | |
| --- | --- | --- | --- | --- | --- | --- |
|  | Absorbency (times) | Dissolution (%) | Absorbency (times) | Absorption rate (seconds) | Lump formation | Gel strength (times) |
| Example 1 | 650 | 7.0 | 80 | 50 | No occurrence | 40 |
| Example 2 | 600 | 6.5 | 78 | 50 | No occurrence | 60 |
| Example 3 | 700 | 7.3 | 82 | 50 | No occurrence | 60 |
| Reference Example 1 | 800 | 19.0 | 85 | 300 | Occurrence | 5 |
| Comparative Example 1 | 800 | 15.0 | 85 | 300 | Occurrence | 5 |
| Comparative Example 2 | 450 | 10.0 | 65 | 120 | To a slight extent | 20 |
| Example 4 | 700 | 7.0 | 85 | 30 | No occurrence | 40 |
| Example 5 | 700 | 6.5 | 85 | 25 | No occurrence | 40 |
| Example 6 | 600 | 6.5 | 78 | 25 | Little | 50 |
| Example 7 | 700 | 6.5 | 82 | 40 | No occurrence | 60 |
| Example 8 | 700 | 7.0 | 80 | 40 | No occurrence | 60 |
| Reference Example 2 | 700 | 16.0 | 83 | 120 | Occurrence | 15 |
| Comparative Example 3 | 800 | 15.0 | 82 | 300 | To a slight extent | 5 |

From the data shown in Table 1, it is seen that the absorbencies for water and physiological saline are for the most part retained in the crosslinked polymers produced in the examples given for illustrating the invention, which reductions in dissolution into water, that lump formation does not take place but significantly increased rates of absorption are attained when said crosslinked polymers are brought into contact with physiological saline, and that the swollen gels resulting from absorption of physiological saline show very great strength. In summary, it is seen that said crosslinked polymers have those performance characteristics which are required of highly water-absorbing resins.

On the contrary, it is seen that the products of the comparative examples as obtained by crosslinking with a hydrophilic polyfunctional epoxy compound are inferior to the products obtained in the examples illustrative of the invention with respect to suppression of dissolution into water, prevention of lump formation, rate of absorption and gel strength, although they are satisfactory in respect of absorbency.

What is claimed is:

1. A resin product having a high water absorbing capability prepared by the process comprising reacting 0.001–0.1 part by weight of an oil soluble polyfunctional alicyclic epoxy compound having the structural formula

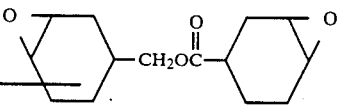

at 50–200° C. with 100 parts by weight of a polymer obtained by reverse-phase suspension polymerization of a monomer composition consisting essentially of an ethylenically unsaturated monocarboxylic acid and/or an alkali metal salt thereof.

* * * * *